United States Patent
Lynch et al.

(10) Patent No.: US 12,259,241 B2
(45) Date of Patent: Mar. 25, 2025

(54) SYSTEMS, METHODS AND COMPUTER PROGRAM PRODUCTS FOR OPTIMIZING OPTICS OF A SURGICAL MICROSCOPE HAVING AN INTEGRATED IMAGING SYSTEM

(71) Applicant: Leica Microsystems NC, Inc., Durham, NC (US)

(72) Inventors: Eric Lynch, Apex, NC (US); Hansford Hendargo, Durham, NC (US); Robert H. Hart, Cary, NC (US)

(73) Assignee: LEICA MICROSYSTEMS NC, INC., Durham, NC (US)

( * ) Notice: Subject to any disclaimer, the term of this patent is extended or adjusted under 35 U.S.C. 154(b) by 291 days.

(21) Appl. No.: 17/904,835

(22) PCT Filed: Mar. 9, 2021

(86) PCT No.: PCT/US2021/021498
§ 371 (c)(1),
(2) Date: Aug. 23, 2022

(87) PCT Pub. No.: WO2021/183508
PCT Pub. Date: Sep. 16, 2021

(65) Prior Publication Data
US 2023/0107680 A1     Apr. 6, 2023

Related U.S. Application Data

(60) Provisional application No. 62/987,481, filed on Mar. 10, 2020.

(51) Int. Cl.
*G01B 9/02055*     (2022.01)
*A61B 3/12*     (2006.01)
*G02B 21/00*     (2006.01)

(52) U.S. Cl.
CPC ........ *G01B 9/02072* (2013.04); *A61B 3/1225* (2013.01); *G02B 21/0012* (2013.01)

(58) Field of Classification Search
CPC ............ G01B 9/02072; G01B 9/02091; G01B 9/02071; G01B 9/02054; G01B 9/02064;
(Continued)

(56) References Cited

U.S. PATENT DOCUMENTS 6,006,128 A * 12/1999 Izatt ..................... A61B 5/0073
600/476
2014/0125952 A1     5/2014 Buckland et al.
(Continued)

FOREIGN PATENT DOCUMENTS

JP     2005-034285 A     2/2005
JP     2009-230141 A     10/2009
(Continued)

OTHER PUBLICATIONS

Notification of Transmittal of the International Search Report and the Written Opinion of the International Searching Authority, or the Declaration, PCT/US2021/021498, Jun. 18, 2021, 10 pages.

*Primary Examiner* — Hoa Q Pham
(74) *Attorney, Agent, or Firm* — LEYDIG, VOIT & MAYER, LTD.

(57) ABSTRACT

A system for optimizing optics is provided. The system is configured to calibrate a position of a reference arm of an interferometric imaging system such that an image of a sample is visible when the sample is positioned at a working distance of an objective lens to provide an initial calibrated position. An image is obtained using the initial calibrated position. Image quality of the obtained image is assessed to determine if the obtained image is a valid image. A path length of the reference arm is adjusted if it is determined that the obtained image is not a valid image. A difference between the calibrated position of the reference arm and the (Continued)

adjusted position of the reference arm is calculated. System elements are adjusted based on the calculated difference such that the sample is visible when the sample is positioned at the working distance at the adjusted position.

26 Claims, 12 Drawing Sheets

(58) Field of Classification Search
CPC ............ G01B 9/02063; G01B 11/2441; A61B 3/0058; A61B 3/1225; A61B 3/13; A61B 3/102; A61B 3/1025; A61B 3/0025; A61B 5/0066; A61B 5/0073; A61B 1/00057; A61B 2090/309; G02B 21/0012; G02B 21/244; G02B 21/274; G02B 21/45

USPC ........ 600/473, 476, 479–480, 309–310, 407; 250/216, 559.4, 363.04; 351/245–246, 351/206, 208; 356/479

See application file for complete search history.

(56) References Cited

U.S. PATENT DOCUMENTS

| | | | |
|---|---|---|---|
| 2015/0031993 A1* | 1/2015 | Buckland | A61B 3/102 |
| | | | 600/425 |
| 2017/0280989 A1 | 10/2017 | Heeren | |
| 2023/0263368 A1* | 8/2023 | Brushett | A61B 5/0066 |

FOREIGN PATENT DOCUMENTS

| | | |
|---|---|---|
| JP | 2011-147612 A | 8/2011 |
| JP | 2017-153542 A | 9/2017 |
| WO | 2019/181553 A1 | 9/2019 |

* cited by examiner

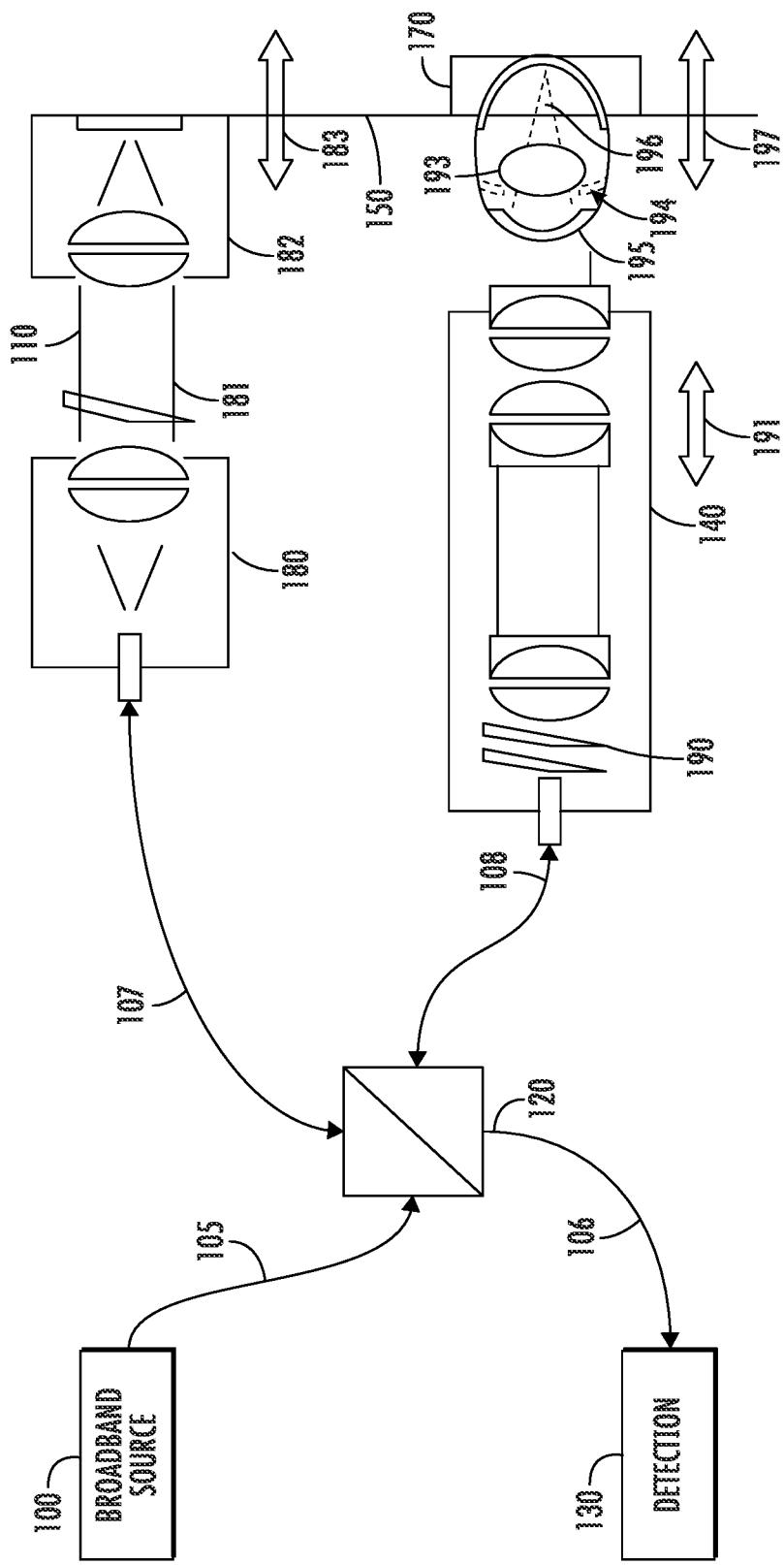

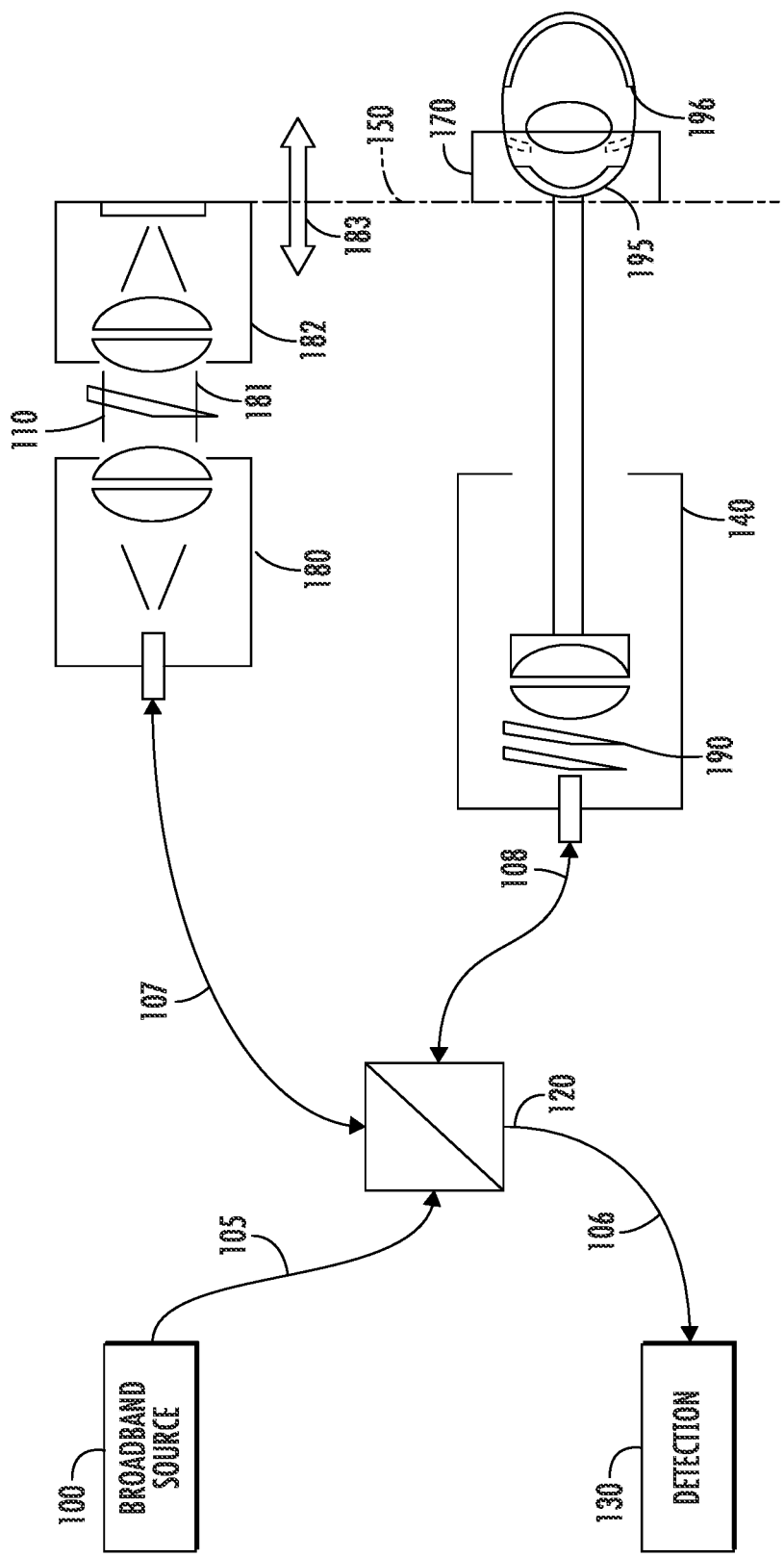

SYSTEMS, METHODS AND COMPUTER PROGRAM PRODUCTS FOR OPTIMIZING OPTICS OF A SURGICAL MICROSCOPE HAVING AN INTEGRATED IMAGING SYSTEM

CROSS-REFERENCE TO RELATED APPLICATIONS

The present application is a U.S.C. § 371 national phase application of PCT International Application No. PCT/US2021/021498, filed Mar. 9, 2021, which claims priority to U.S. Provisional Patent Application No. 62/987,481, filed Mar. 10, 2020. The disclosures of each are hereby incorporated herein by reference in their entireties.

FIELD

The present inventive concept relates generally to imaging and, more particular, to microscopes having integrated OCT systems and related systems and methods.

BACKGROUND

Use of optical coherence tomography (OCT) during, for example, eye surgery generally requires that an OCT system be integrated with a surgical microscope. Surgical microscopes provide a magnified view of the operating field to the surgeon. Ophthalmic surgical microscopes are commonly stereo zoom microscopes with binocular view ports for the surgeon, and frequently have one or two observer view ports at ninety degrees (left and right) to the surgeon. A "working distance" is provided between the objective lens of the microscope and the surface of a patient eye (sample) in order to allow the surgeon sufficient working area.

Integration of the surgical microscope with OCT can lead to at least two different optical systems within the microscope, one for the OCT system, and one for the standard white light imaging path through the microscope oculars. To obtain ideal image quality across each modality, the microscope is generally parfocal, i.e. each optical sub-system has a matched focal point which should correspond to the focal plane of the objective lens as illustrated, for example, in FIG. 1. Thus, FIG. 1 represents a focal plane of a microscope objective lens with an ideal working distance (WD) when measured from the last glass surface of lens.

Due to the presence of multiple optical components in the white light path, it is possible to set the microscope objective at a position other than the working distance and still obtain an image that appears to be in focus by compensating with other system components, such as the ocular eyepieces. For example, FIG. 2 illustrates a working distance (WDshort) that is set too short by compensating using viewing ocular lens diopter adjustment. FIG. 3 illustrates a working distance (WDlong) that is set too long by compensating using viewing ocular lens diopter adjustment. Use of systems shown in FIGS. 2 and 3 may lead to a lower quality OCT image as the sample may be out of focus with respect to the microscope objective lens, which would also be true for additional imaging modalities that might be added onto the microscope.

OCT systems are designed to have optimal image quality at the working distance of the microscope objective as shown in FIG. 4. FIG. 4 illustrates an OCT system having an imaging plane set to match the focal plane of the objective lens. OCT uses the principles of low coherence interferometry to obtain three-dimensional (3D) images of a sample. The optical path length through the sample arm of the OCT system is generally matched by the optical path through the reference arm of the OCT system, which typically consists of a mirror mounted on a translatable stage. A specific position of this reference mirror in the reference arm generally maps to the working distance of the microscope objective. If the sample is placed at a position other than the working distance of the microscope objective, the reference mirror is moved a corresponding distance to ensure the optical path lengths are matched. Initial calibration of the reference arm position to the working distance allows deviations from this position to be detected. Conventional methods for adjusting the elements of the system are generally trial and error, i.e. no specific coordinates are provided for the adjustments made.

SUMMARY

Some embodiments of the present inventive concept provide a system for optimizing optics of a surgical microscope having an integrated imaging system. The system includes one or more processors and one or more storage devices; a first optical system associated with the surgical microscope; and a second optical system, different from the first optical system, associated with an interferometric imaging system, such as OCT. The system is configured to calibrate a position of a reference arm of the imaging system such that an image of a sample is visible when the sample is positioned at a working distance of an objective lens of the surgical microscope to provide an initial calibrated position. The system is further configured to obtain an image using the initial calibrated position of the reference arm of the imaging system. Image quality of the obtained image is assessed to determine if the obtained image is a valid image of the intended sample target. A path length of the reference arm of the imaging system is adjusted if it is determined that the obtained image is not a valid sample target image until it is determined that the obtained image is a valid image to provide an adjusted position of the reference arm. A difference between the original calibrated position of the reference arm and the adjusted position of the reference arm is calculated. Elements of the system are adjusted based on the calculated difference such that the sample is visible when the sample is positioned at the working distance of the objective lens of the surgical microscope at the adjusted position of the reference arm.

In some embodiments, the system may be further configured to determine if the imaging system is in focus at the adjusted position of the reference arm before adjusting the elements of the system. The elements of the system may be adjusted when it is determined that the system is not in focus until it is determined that the imaging system is in focus.

In further embodiments, the system may be further configured to repeatedly adjust the path length of the reference arm of the imaging system, calculate the difference between the current reference arm position and the original calibrated position, and adjust the elements of the system until it is determined that the system is in focus.

In still further embodiments, the system may be further configured to determine if the obtained image contains a valid image of the sample target based on one of signal quality and features present or absent from the obtained image.

In some embodiments, an imaging plane of the imaging system may match a focal plane of the surgical microscope when the system is in focus.

In further embodiments, the system may be further configured to adjust elements of the system by adjusting at least one of the eye pieces associated with the surgical microscope and other optical components of the system.

In still further embodiments, the system may be further configured to adjust a position of the reference arm by adjusting a mirror in the reference arm to provide matching optical path lengths in the reference arm and a sample arm of the imaging system and the working distance such that the sample is visible when the sample is positioned at the working distance of the objective lens of the surgical microscope.

In some embodiments, the working distance of the objective lens of the surgical microscope may be a distance between an objective lens of the surgical microscope and a surface of a sample.

In further embodiments, the imaging system may be one of an optical coherence tomography (OCT) imaging system.

In still further embodiments, the system may be configured to adjust the path length of the reference arm of the imaging system and/or the elements of the system manually.

In some embodiments, the system may be further configured to adjust the path length of the reference arm of the imaging system and/or the elements of the system automatically.

In further embodiments, the system may further include a reducing lens between the objective lens and the sample to reduce a focal length of the objective lens. A relay lens may be provided adjacent the sample to relay an objective lens image plane to a retina of the sample to adapt the system for imaging the retina of the sample.

In still further embodiments, the objective lens may be a multifocal objective lens and the system may further include a relay lens adjacent the sample to relay an objective lens image plane to a retina of the sample to adapt the system for imaging the retina of the sample.

Some embodiments of the present inventive concept provide a method for optimizing optics of a surgical microscope having an integrated imaging system, the system including one or more processors and one or more storage devices; a first optical system associated with the surgical microscope; and a second optical system, different from the first optical system, associated with the imaging system. The method includes calibrating a position of a reference arm of the imaging system such that an image of a sample is visible when the sample is positioned at a working distance of an objective lens of the surgical microscope to provide an initial calibrated position; obtaining an image using the initial calibrated position of the reference arm of the imaging system; accessing image quality of the obtained image to determine if the obtained image is a valid image; adjusting a path length of the reference arm of the imaging system if it is determined that the obtained image is not a valid image until it determined that the obtained image is a valid image to provide an adjusted position of the reference arm; calculating a difference between the original calibrated position of the reference arm and the adjusted position of the reference arm; and adjusting elements of the system based on the calculated difference such that the sample is visible when the sample is positioned at the working distance of the objective lens of the surgical microscope at the adjusted position of the reference arm.

Related computer program products are also provided.

BRIEF DESCRIPTION OF THE DRAWINGS

FIG. 5A is a block diagram illustrating an example OCT retinal (posterior) imaging system.

FIG. 5B is a block diagram illustrating an example OCT cornea (anterior) imaging system.

DETAILED DESCRIPTION

Figure 2:
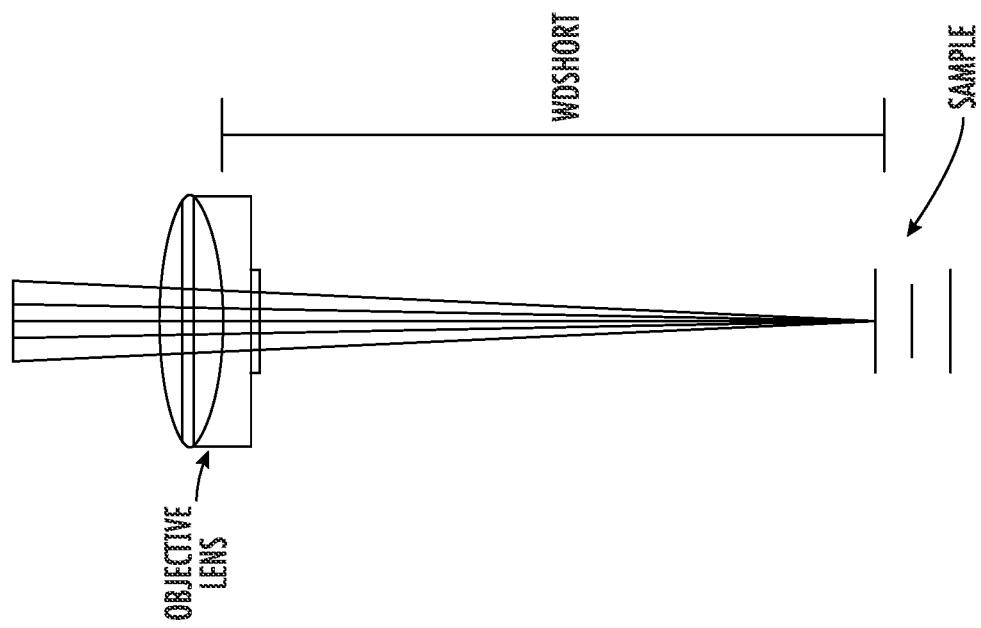
FIG. 2 is a diagram of a focal plane of a microscope objective lens illustrating a working distance that is set too short.
Figure 1:
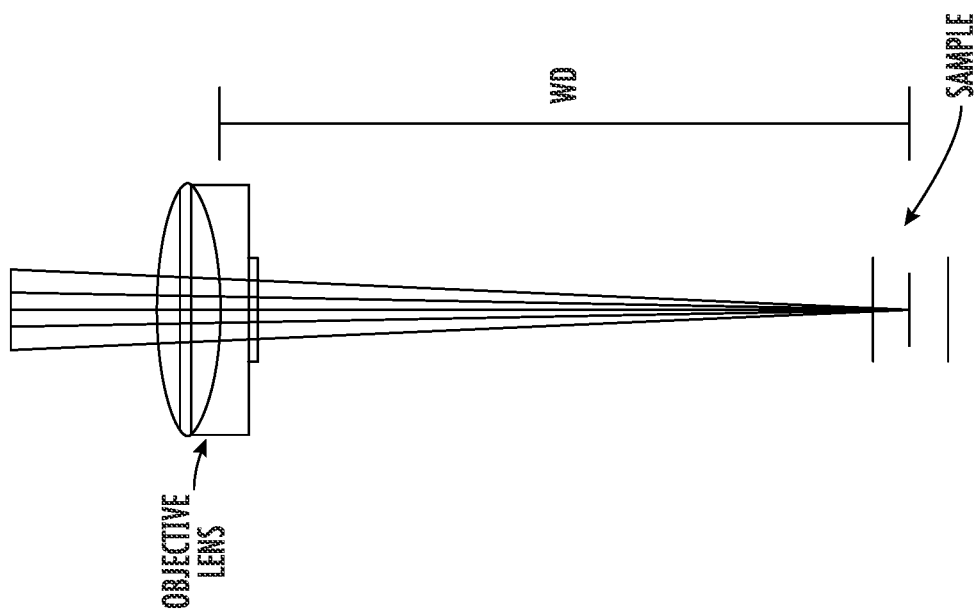
FIG. 1 is a diagram of a focal plane of a microscope objective lens illustrating a proper "working distance."

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks. As used herein, "a processor" may refer to one or more processors.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

As used herein, "subject" refers to a person or thing or a portion of a person or thing being imaged. It will be understood that although embodiments of the present inventive concept are discussed herein with respect to an eye being the subject, embodiments of the present inventive concept are not limited to this configuration. The subject can be any subject, including, for example, veterinary, cadaver study or human subject without departing from the scope of the present inventive concept.

Although many of the examples discussed herein refer to the sample/subject being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

Although embodiments of the present inventive concept focus on the use of OCT to scan the sample, embodiments of the present inventive concept are not limited to the use of OCT. It will be understood that any method and system that used to scan a sample can be used without departing from the scope of the present inventive concept.

Furthermore, imaging as discussed herein can be performed in any manner known to those having skill in the art. For example, in some embodiments the imaging system may be incorporated into a microscope or surgical microscope. Various of these embodiments are discussed in, for example, U.S. Pat. No. 8.77,412 and U.S. Patent Publication Nos. 2015/0168250 and 2015/0359426, the disclosures of which are incorporated herein by reference as if set forth in its entirety.

As used herein, a "working distance" refers to a distance from a last glass surface of an objective lens to a surface of the sample. The working distance may be referred to as WD throughout this specification.

Systems in accordance with some embodiments of the present inventive concept include a microscope including both a surgical optical system (first optical system) and a second-interferometric-based optical system (second optical system). In some embodiments, the interferometric-based optical system is an OCT imaging system. However, embodiments of the present inventive concept are not limited thereto. For example, as used herein an "interferometric imaging system" refers to an imaging system utilizing optical signals generated from the interference of light between a reference and a sample optical path. Some embodiments may further include one or more additional imaging systems that have a separate optical path in the microscope, but shares the same objective. For example, these additional imaging systems may be fundus fluorescence, scanning laser ophthalmoscope, widefield imaging systems, and the like, without departing from the scope of the present inventive concept.

Example interferometric imaging systems for use in accordance with some embodiments of the present inventive concept will now be discussed with respect to FIGS. 5A and 5B. It will be understood that these systems are provided for example purposes only and, thus, embodiments of the present inventive concept should not be limited thereto. Conventional Fourier domain OCT (FDOCT) systems will now be discussed to provide some background related to these systems. Referring first to FIG. 5A, a block diagram of an FDOCT retinal imaging system will be discussed. As illustrated in FIG. 5A, the system includes a broadband source 100, a reference arm 110 and a sample arm 140 coupled to each other by a beamsplitter 120. The beamsplitter 120 may be, for example, a fiber optic coupler or a bulk or micro-optic coupler. The beamsplitter 120 may provide from about a 50/50 to about a 90/10 split ratio. As further illustrated in FIG. 5A, the beamsplitter 120 is also coupled to a wavelength or frequency sampled detection module 130 over a detection path 106 that may be provided by an optical fiber.

As further illustrated in FIG. 5A, the source 100 is coupled to the beamsplitter 120 by a source path 105. The source 100 may be, for example, a continuous wave broadband superluminescent diode, a pulsed broadband source, or tunable source. The reference arm 110 is coupled to the beamsplitter 120 over a reference arm path 107. Similarly, the sample arm 140 is coupled to the beamsplitter 120 over the sample arm path 108. The source path 105, the reference arm path 107 and the sample arm path 108 may all be provided by optical fiber or a combination of optical fiber, free-space, and bulk- or micro-optical elements.

As illustrated in FIG. 5A, the reference arm of the FDOCT retinal imaging system may include a collimator assembly 180, a variable attenuator 181 that may include a neutral density filter or a variable aperture, a mirror assembly 182, a reference arm variable path length adjustment 183 and a path length matching position 150, i.e. optical path length matching between the reference arm path length and the sample arm path length to the subject region of interest. As further illustrated, the sample arm 140 may include a dual-axis scanner assembly 190 and an objective lens with variable focus 191.

The sample illustrated in FIG. 5A is an eye including a cornea 195, iris/pupil 194, ocular lens 193 and retina 196. A representation of an FDOCT imaging window 170 is illustrated near the retina 196. The retinal imaging system relies on the objective lens plus the optics of the subject eye, notably cornea 195 and ocular lens 193, to image the posterior structures of the eye. As further illustrated the region of interest 170 within the subject is selected through coordination of the focal position 196 and reference arm path length adjustment 183, such that the path length matching position 197 within the subject is at the desired location.

Referring now to FIG. 5B, a block diagram illustrating a FDOCT corneal (anterior) imaging system will be discussed. As illustrated therein, the system of FIG. 5B is very similar to the system of FIG. 5A. However, the objective lens variable focus need not be included, and is not included in FIG. 5B. The anterior imaging system of FIG. 5B images the anterior structures directly, without reliance on the optics of the subject to focus on the anterior structures.

Figure 4:
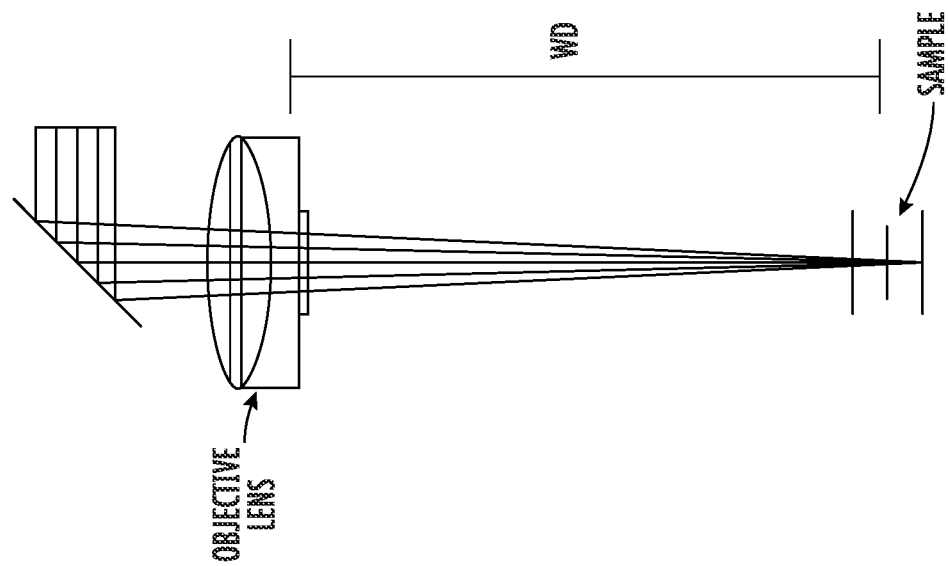
FIG. 4 is a diagram illustrating a system having an OCT imaging plane set to match the focal plane of the objective lens.

As discussed in the background above, OCT systems are designed to have optimal image quality at the working distance WD of the microscope objective as shown in FIG. 4. The optical path length through the sample arm of the OCT system is generally matched by the optical path through the reference arm of the OCT system, which typically consists of a mirror mounted on a translatable stage. As used herein, "optical path length (OPL)" refers to a geometric length of the path followed by light through a given system multiplied by the optical index of refraction for the concurrent medium through which the light travels. A specific position of this reference mirror in the reference arm generally maps to the working distance of the microscope objective. If the sample is placed at a position other than the working distance of the microscope objective, the reference mirror is moved a corresponding distance to ensure the optical path lengths are matched. Initial calibration of the reference arm position to the working distance allows deviations from this position to be detected. Conventional methods for adjusting the elements of the system are generally trial and error, i.e. no specific coordinates are provided for the adjustments made.

Accordingly, some embodiments of the present inventive concept provide methods and systems for detecting the presence of a valid OCT image of a sample target, setting the OCT reference arm at a position to detect the image and optimizing the optics of multiple optical subsystems to obtain a best possible image. In other words, instead of the trial and error conventional methods, embodiments of the present inventive concept use OCT to measure where the target is and then tell the system operator where to go based on the OCT measurements. In some embodiments, these adjustments may be performed automatically as will be discussed further below.

Figure 6:
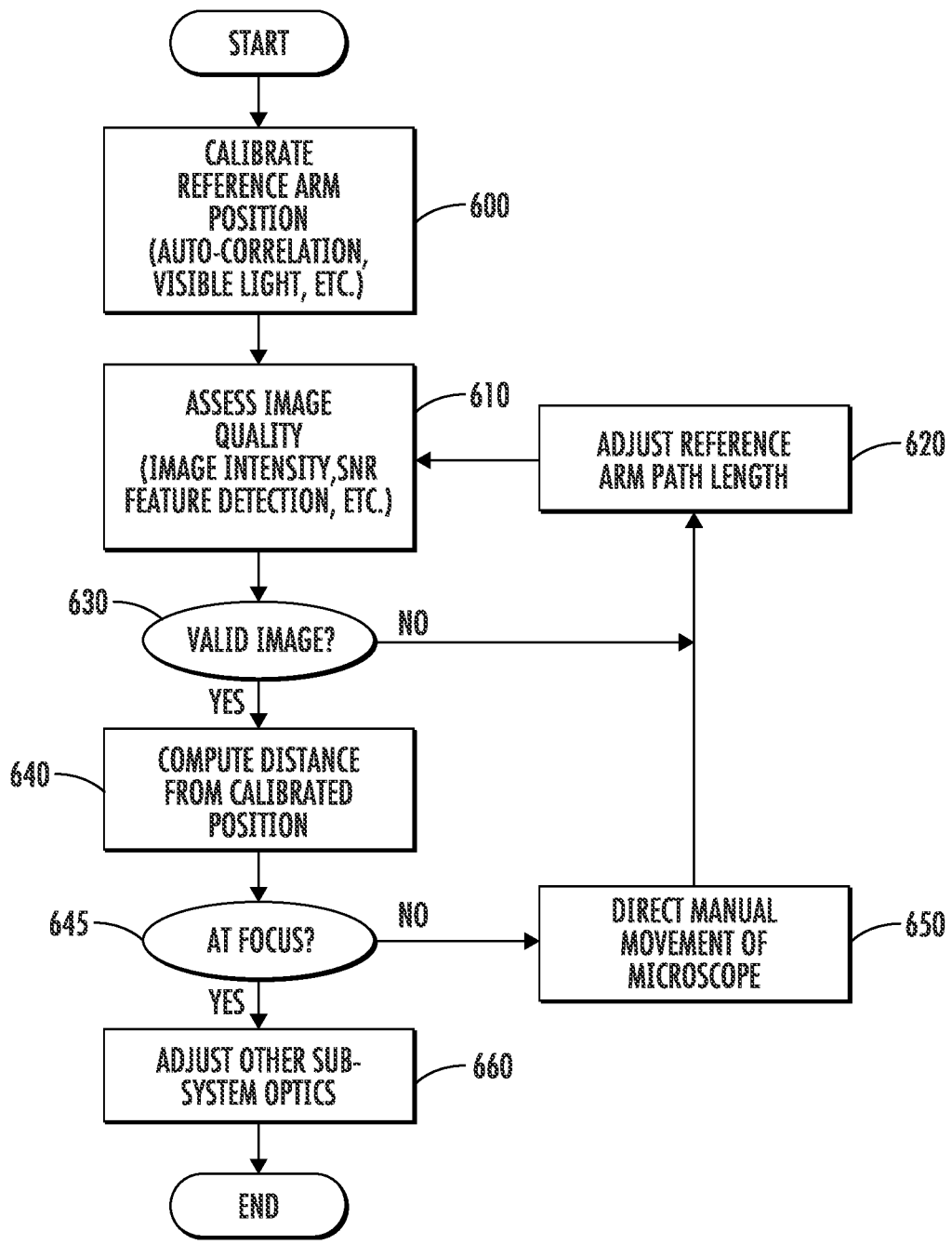
FIG. 6 is a flowchart illustrating operations for optimization using manual adjustments in accordance with some embodiments of the present inventive concept.

Referring now to FIG. 6, a flowchart illustrating operations of detecting the presence of a valid OCT image of a sample target, setting the OCT reference arm at a position to detect the image, and optimizing the optics of multiple optical sub-systems to obtain the best image quality will be discussed. As illustrated in FIG. 6, operations for optimization using manual adjustments of the microscope begin at block 600 by calibrating a reference arm of the system. A factory or service calibration of the instrument may be performed. The OCT reference arm is set to a distance such that the OCT image of a sample target is visible when the target (sample) is positioned at the working distance of the microscope objective as shown in, for example, FIG. 4. Conventionally, the target is first viewed through the microscope visible light path set at infinity focus and maximum magnification to ensure that the target is accurately positioned at the focal plane of the microscope objective lens. This is a subjective technique and can therefore lead to inaccuracies. Thus, in accordance with some embodiments of the present inventive concept, methods discussed herein are used to increase the likelihood that the target is placed at the exact (substantially) focal plane of the objective lens. It will be understood that the "exact" location refers to a location as close a possible to the exact location, as the exact location may be impossible to achieve. As used herein, "focal plane" refers to the distance from the objective lens at which collimated light collected over the aperture of the lens converges together.

The signal used to generate an OCT image can be created from interference between light in the sample and reference arms (cross-correlation signal) or from light interfering between different optical reflectors in a single arm (auto-correlation signal). The optical path lengths in the reference and sample arms must be closely matched to be within the detection bandwidth of the optical detector of the system to generate a cross-correlation signal. To view the auto-correlation signal, light must be sufficiently focused on a sample to generate enough optical signal strength from a single arm. The Fourier transform of the auto-correlation signal results in signal near zero frequency and is affected by the same signal fall-off effects as the cross-correlation signal. The auto-correlation signal provides a means to determine whether a sample is at the focal plane of the microscope objective. Light from the reference arm may either be blocked or the reference arm moved to a position to move the cross-correlation signal beyond the detection bandwidth of the system. A collimated (parallel) OCT beam may be injected through the objective lens and an assessment is made of the maximum signal strength of the OCT auto-correlation signal generated by reflected light from the target to determine whether the sample is at the correct position. The focus of the microscope objective is adjusted to increase, or possibly, maximize, this signal. This may entail moving the position of the objective or adjusting optical elements to shift the focal plane of the objective and can be done either manually or in an automated manner. The assessment of the auto-correlation signal may include analysis of the signal-to-noise ratio or intensity strength of the Fourier transform magnitude near zero frequency. Once the auto-correlation is maximized, the reference path is adjusted until the OCT cross-correlation signal is visible and positioned near the zero-frequency position within the OCT B-Scan.

Once calibration has been performed (block 600), an image is detected, and the quality of the image is assessed (block 610). For example, the presence of a valid OCT image is detected via software algorithms that assess the signal quality or detect specific features within a given OCT image. In some embodiments, these methods may include, but are not limited to, maximum intensity, intensity distribution, or variance of intensity throughout the image, the signal-to-noise ratio of the image, or detection of specific sample target features through machine learning or classical object detection methods. It is determined if a valid OCT image is present (block 630). If a valid image is not present (block 610), the reference arm is moved through a series of positions (block 620) until a position is found that yields a valid OCT image (block 630). Other system optics affecting beam focus, polarization, or other factors that may affect image quality are adjusted to optimize OCT signal strength and may be done sequentially or simultaneously with reference arm movement. If it is determined that a valid image is present (block 630), a difference from the calibrated reference arm position with respect to the microscope working distance is calculated (block 640).

It is determined if the microscope is focused (block 645). If it is determined that the microscope is not focused (block 645), manual adjustments may be made (block 650) until it is determined that the microscope is focused (block 645). Once focused (block 645) operations may proceed to block 660 where other subsystem optics may be adjusted. For example, the user can be instructed to adjust the other optical components, i.e., microscope eye pieces, that may affect the image quality to ensure parfocality (focal points in the same plane) across each imaging modality integrated with the microscope. Should other imaging modalities, for example, fluorescence microscope, scanning laser ophthalmoscope, and the like, be included in the microscope, this information could also be used to optimize the focus of related optics for improved image quality without departing from the scope of the present inventive concept. In other words, any other additional imaging system that has a separate optical path in the microscope, but shares the same objective lens could be used without departing from the scope of the present inventive concept. For example, fundus fluorescence, scanning laser ophthalmoscope, widefield imaging systems, and the like.

Figure 7:
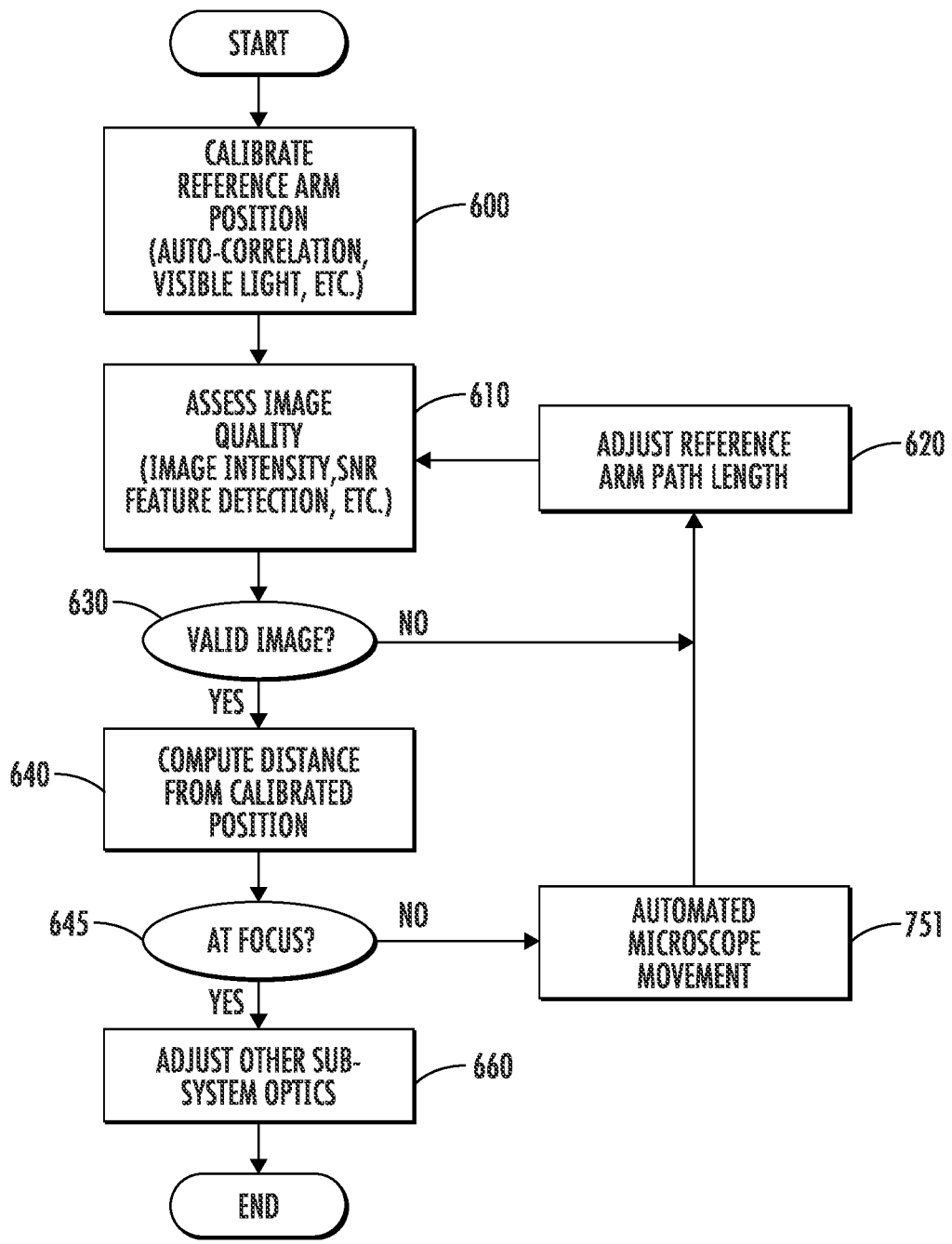
FIG. 7 is a flowchart illustrating operations for optimization using automated adjustments in accordance with some embodiments of the present inventive concept.

Although embodiments of the present inventive concept illustrated in FIG. 6 illustrate manual adjustment of the microscope (block 650), embodiments of the present inventive concept are not limited to this configuration. FIG. 7 illustrates similar operation to the operations discussed above with respect to FIG. 6, thus, details of the blocks will not be repeated herein in the interest of brevity. However, as illustrated in FIG. 7, instead of manual microscope movement, block 751 of FIG. 7 indicates that the movement of the microscope may be automatic. Thus, systems in accordance with embodiments discussed herein may be programmed to adjust automatically without departing from the scope of the present inventive concept. For example, the microscope working distance can be automatically adjusted as shown in FIG. 7 or information can be conveyed to the user on the direction and distance with which to move the microscope as shown in FIG. 6.

Figure 8:
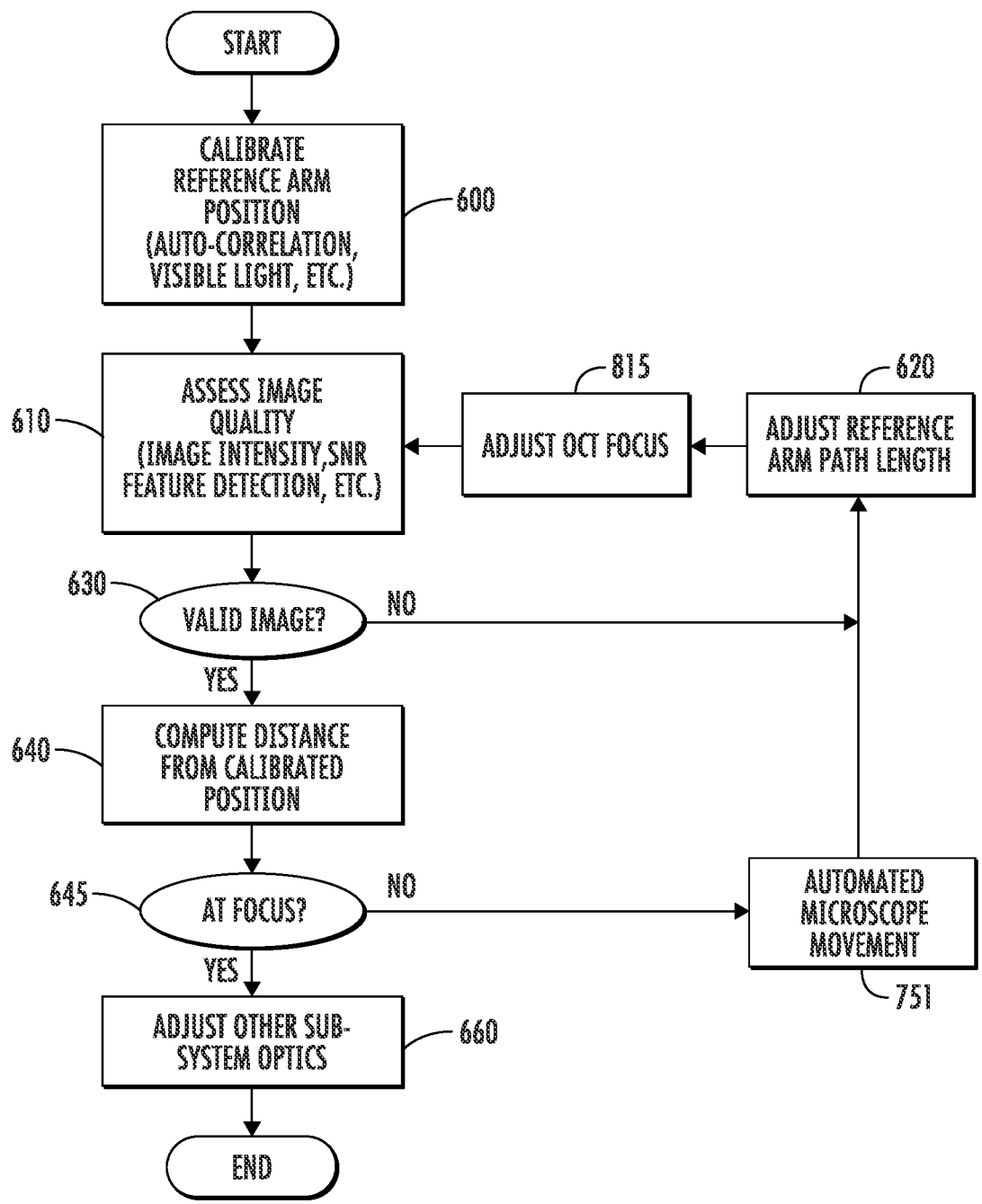
FIG. 8 is a flowchart illustrating operations for automated microscope movement and OCT focus adjustments in accordance with some embodiments of the present inventive concept.
Figure 9:
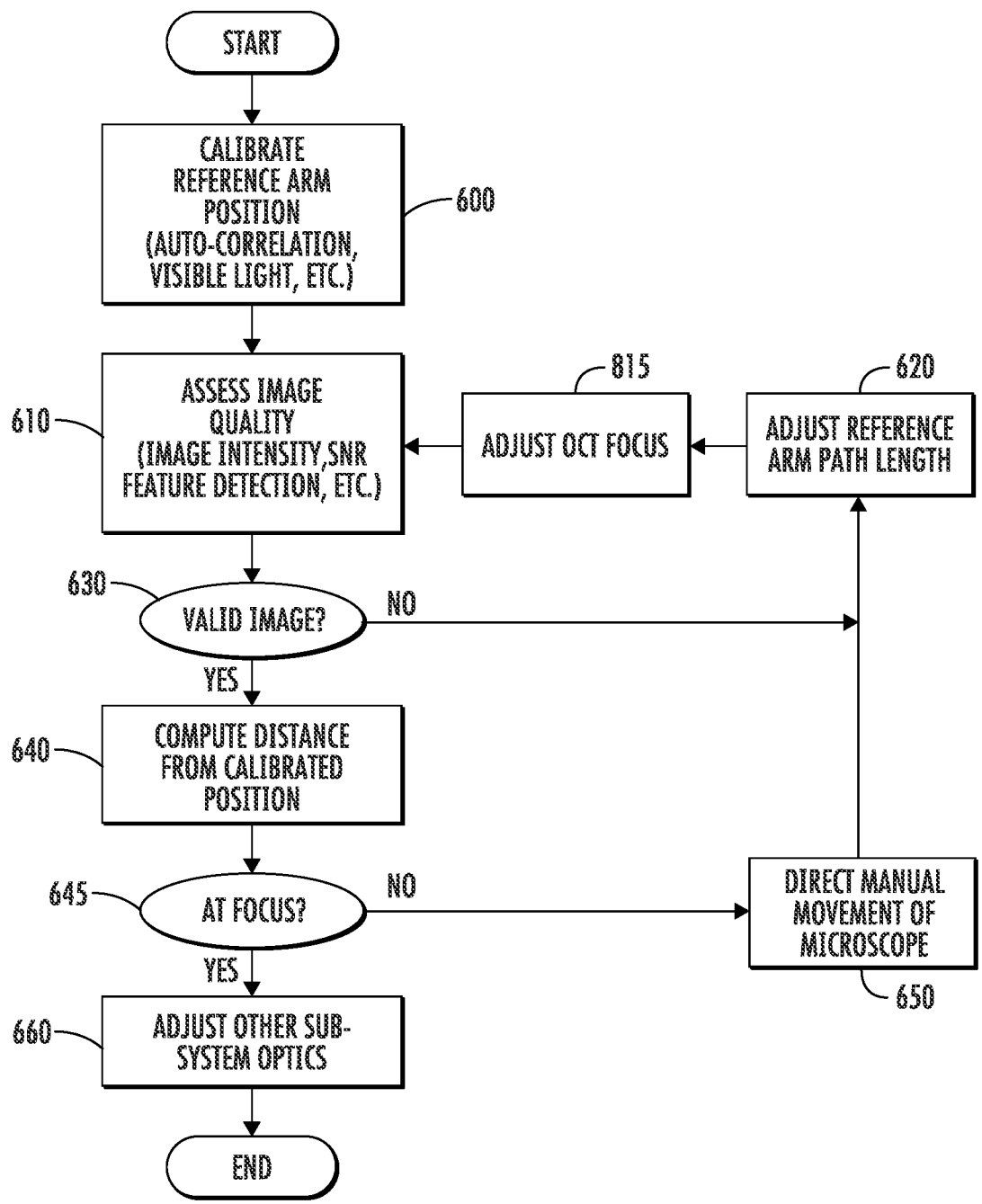
FIG. 9 is a flowchart illustrating operations for manual microscope movement and OCT focus adjustments in accordance with some embodiments of the present inventive concept.

Referring now to the flowcharts of FIGS. 8 and 9, the flowcharts are very similar to the flowcharts of FIGS. 6 and 7. Thus, details with respect to like elements will not be repeated in the interest of brevity. In addition to the details discussed in FIG. 7, FIG. 8 includes an OCT focus adjustment (block 815) responsive to a determination that the image is not valid (block 630). Thus, when the image is determined to be invalid (block 630), the reference arm path length is adjusted (block 620) and the OCT focus is adjusted (block 815). The remaining operations proceed as discussed above with respect to FIG. 7 having automated microscope adjustments (block 751). The flowchart of FIG. 9 adds a same OCT adjustment (block 815) to a manual microscope adjustment (block 650) discussed above with respect to FIG. 6.

Figure 10:
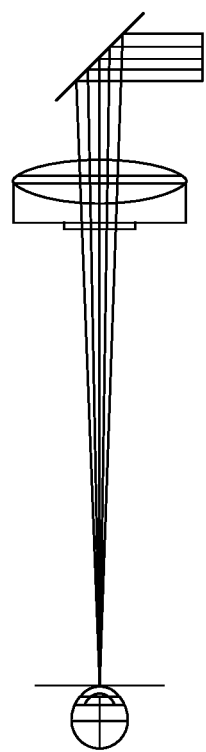
FIG. 10 is a diagram illustrating a microscope objective set for imaging a cornea.
Figure 11:
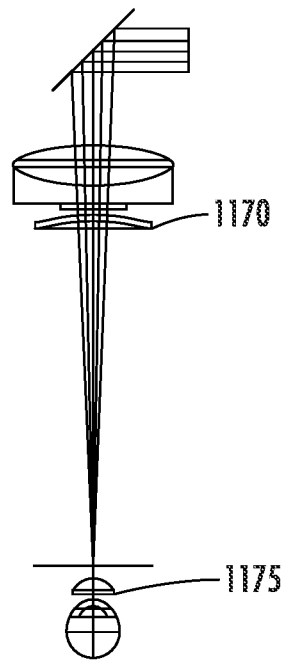
FIG. 11 is a diagram illustrating a retinal view lens system including a reducing lens in combination with a relay lens.

Referring now to FIGS. 10 and 11, adding auxiliary lens systems to the objective set will be discussed. FIG. 10 illustrates a standard microscope objective set for imaging of the cornea. FIG. 11 illustrates a system including a standard retinal view lens system which includes an additional reducing lens and a relay lens. Additional complications may arise when these axillary retinal viewing lens systems are attached to the microscope. These lens systems are generally required to relay the microscope objective lens focal plane from the cornea position to the retina of the eye under surgery. Since standard workflow requires that these imaging systems operate without requiring the microscope position to be moved between cornea imaging and retinal imaging, the relay system consists of two optical elements working together. The first element 1170 (reducing lens) of FIG. 11 effectively reduces the focal length of the microscope objective lens to allow a relay lens 1175 of FIG. 11 to be mechanically positioned within close proximity to the cornea and relay the microscope objective lens image plane to the retina of the eye under surgery.

Figure 3:
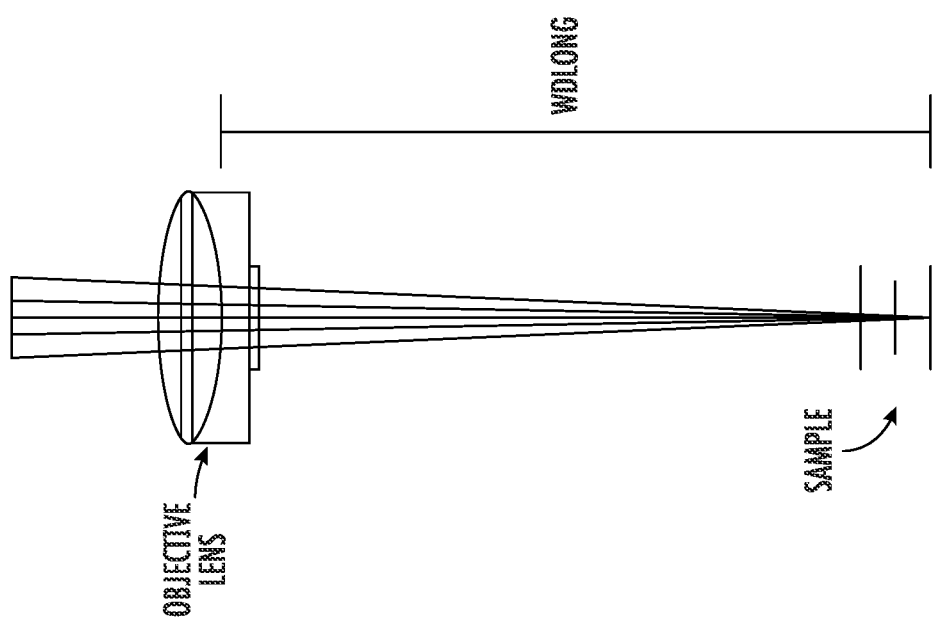
FIG. 3 is a diagram of a focal plane of a microscope objective lens illustrating a working distance that is set too long.
Figure 12:
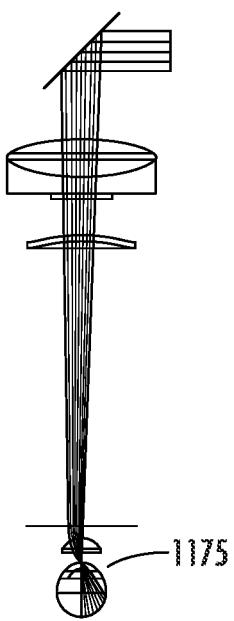
FIG. 12 is a diagram illustrating that wide field of view (FOV) imaging requires close proximity of a retinal relay lens relative to the cornea.

Close proximity of the relay lens 1175 to the cornea is generally required for large field of view (FOV) as shown in FIG. 12. Therefore, if the microscope is improperly setup as discussed above with respect to FIGS. 2 and 3, then adding the retinal viewing system (1170/1175) will result in even further perturbation of the microscope imaging optics from the optimum working distance forcing the other imaging modalities, such as OCT to effectively operate well outside the normal imaging window.

Figure 14:
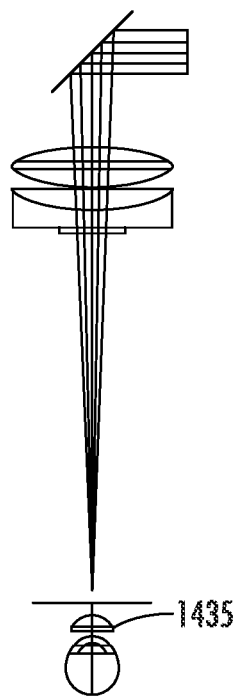
FIG. 14 is a diagram illustrating a system having an extension of the split lens design to include multifocal capability elimination.
Figure 15:
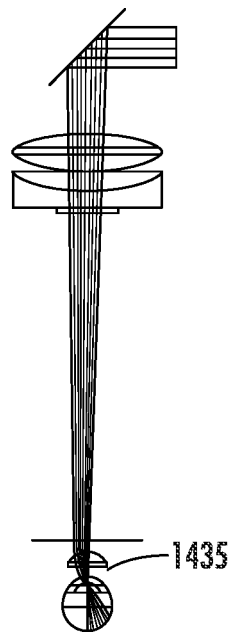
FIG. 15 is a system multifocal design that allows for full retinal FOV imaging.

Further complications arise from the adjustability of the retinal viewing lens system relay lens for accommodation of the refractive error of the eye under surgery. These errors can be compounded in such a way as to produce a non-functional result for additional imaging modalities such as OCT. Some embodiments of the present inventive concept address this situation by providing a multifocal length objective lens as opposed to a fixed focus objective lens and a relay lens 1435 as shown in FIG. 13 through 15.

Figure 13:
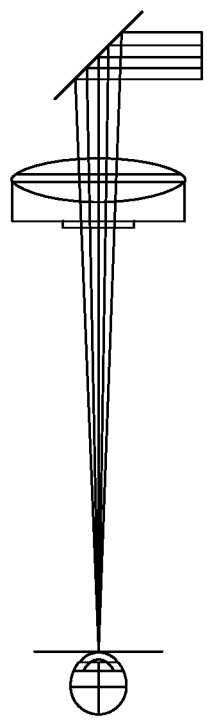
FIG. 13 is a diagram of a microscope objective lens design consisting of split elements.

Current microscope lens design uses split elements as a method to reduce optical aberrations in the image as depicted in FIG. 13. Extending this concept to allow for the air space between elements to be increased or decreased allows for adjustability of the overall lens focal length. FIG. 14 illustrates that increasing the air space between elements will shorten the focal length allowing a retinal viewing relay lens 1435 to be used for imaging the retina without the need for a secondary reduction lens as shown in the standard configuration of FIG. 11. FIG. 15 illustrates that a multifocal design may allow for full retinal field of view imaging.

Furthermore, adjusting the air space between elements can accommodate the refractive error of the eye under surgery. One advantage to using a multifocal objective design is that since the optical path of all imaging modalities are co-aligned through the objective lens the requirement for individual focus adjustability between optical paths is effectively eliminated.

Independent feedback from an external distance rangefinder can also be incorporated in the positioning control loop to further reduce the risk of patient eye impact from the retinal relay lens.

Figure 16:
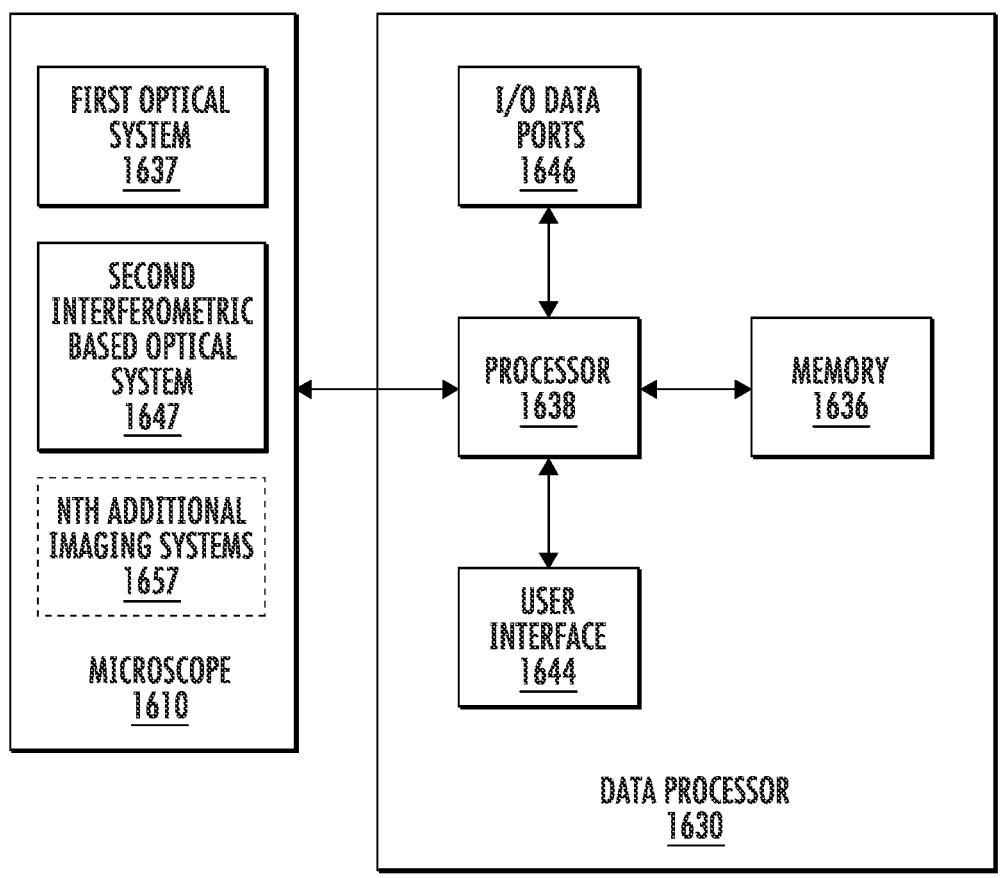
FIG. 16 is a block diagram of a data processing system that may be used to implement processes in accordance with various embodiments of the present inventive concept.

As is clear from the discussion of embodiments of the present inventive concept above, many of the methods discussed herein require processing provided by a computing device. Referring now to FIG. 16, example embodiments of a data processing system 1630 configured in accordance with embodiments of the present inventive concept will be discussed with respect to FIG. 16. As will be understood, the data processing system may be included in the system of, for example, FIGS. 5A and 5B, in a microscope, or may be a separate device that communicates with the system in FIGS. 5A and 5B or the microscope without departing from the scope of the present inventive concept. The data processing system 1630 may include a user interface 1644, including, for example, input device(s) such as a keyboard or keypad, a display, a speaker and/or microphone, and a memory 1636 that communicate with a processor 1638. The data processing system 1630 may further include I/O data port(s) 1646 that also communicates with the processor 1638. The I/O data ports 1646 can be used to transfer information between the data processing system 1630 and another computer system or a network using, for example, an Internet Protocol (IP) connection. These components may be conventional components such as those used in many conventional data processing systems, which may be configured to operate as described herein.

As further illustrated in FIG. 16, the data processing system 1630 communicates with the microscope 1610 which includes a first optical system 1637, a second interferometric optical system 1647 and optionally one or more additional systems 1657 (the dotted lines in FIG. 16 indicate an optional element(s)). The first optical system 1637 may be associated with the microscope, the second-interferometric-based optical system 1647 may be provided by an OCT imaging system as discussed above. However, embodiments of the present inventive concept are not limited thereto. As further illustrated the additional imaging modalities may also be provided by optional systems associated with the first and second systems. For example, some embodiments may further include one or more additional imaging systems 1657 that have a separate optical path in the microscope, but shares the same objective. For example, these additional imaging systems may be fundus fluorescence, scanning laser ophthalmoscope, widefield imaging systems, and the like, without departing from the scope of the present inventive concept.

Figure 17:
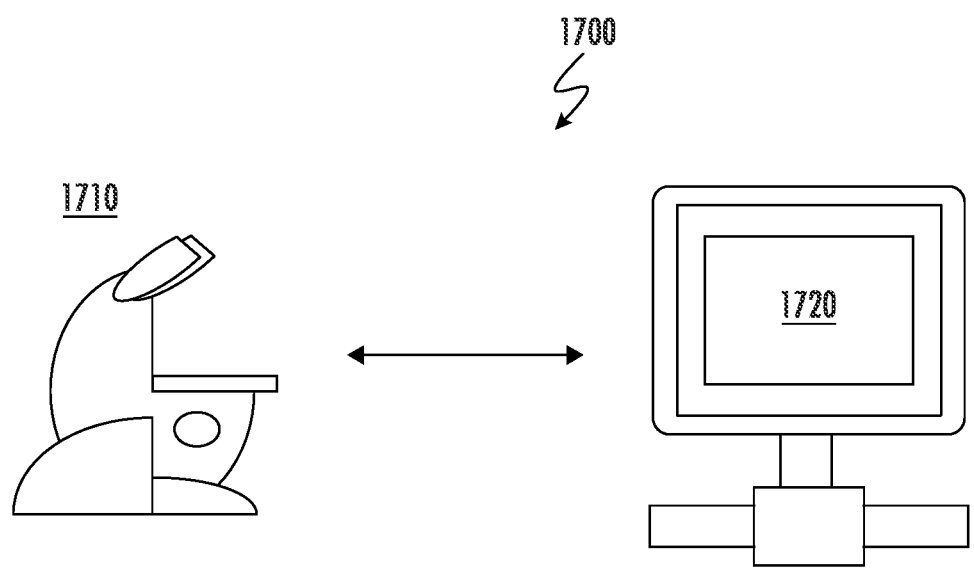
FIG. 17 is block diagram a system in accordance with some embodiments of the present inventive concept including a microscope.

Some embodiments of the present inventive concept relate to a microscope comprising a system as described in connection with one or more of the FIGS. 1 to 16. Alternatively, a microscope may be part of or connected to a system as described in connection with one or more of the FIGS. 1 to 16. FIG. 17 shows a schematic illustration of a system 1700 configured to perform a method described herein. The system 1700 comprises a microscope 1710 and a computer system 1720. The microscope 1710 is configured to take images and is connected to the computer system 1720. The computer system 1720 is configured to execute at least a part of a method described herein. The computer system 1720 may be configured to execute a machine learning algorithm. The computer system 1720 and microscope 1710 may be separate entities but can also be integrated together in one common housing. The computer system 1020 may be part of a central processing system of the microscope 1710 and/or the computer system 1720 may be part of a subcomponent of the microscope 1710, such as a sensor, an actor, a camera or an illumination unit, etc. of the microscope 1710.

The computer system 1720 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 1020 may comprise any circuit or combination of circuits. In one embodiment, the computer system 1-20 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 1720 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 1020 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 1720 may also include a display device, one or more speakers, and a keyboard and/or controller, which can include a mouse, trackball, touch screen, voice-recognition device, or any other device that permits a system user to input information into and receive information from the computer system 1720.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the inventive concept can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the inventive concept comprise a data carrier having electronically readable control signals, which are capable of cooperating with a programmable computer system, such that one of the methods described herein is performed.

Generally, embodiments of the present inventive concept can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present inventive concept is, therefore, a computer program having a program code for performing one of the methods described herein, when the computer program runs on a computer.

A further embodiment of the present inventive concept is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present inventive concept is an apparatus as described herein comprising a processor and the storage medium.

A further embodiment of the inventive concept is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the inventive concept comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The flowchart and block diagrams in the Figures illustrate the architecture, functionality, and operation of possible implementations of systems, methods and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

That which is claimed is:

1. A system for optimizing optics of a surgical microscope having an integrated imaging system, the system comprising:
   one or more processors and one or more storage devices;
   a first optical system associated with the surgical microscope; and
   a second interferometric-based optical system, different from the first optical system, associated with the imaging system, wherein the system is configured to:
   calibrate a position of a reference arm of the second interferometric-based optical system such that an image of a sample is visible as the sample is positioned at a working distance of an objective lens of the surgical microscope to provide an initial calibrated position;
   obtain an image of the sample using the initial calibrated position of the reference arm of the imaging system;
   assess image quality of the obtained image to determine whether the obtained image is a valid image;
   adjust a path length of the reference arm of the imaging system upon determining that the obtained image is not a valid image until it is determined that the obtained image is a valid image to provide an adjusted position of the reference arm;
   calculate a difference between the initial calibrated position of the reference arm and the adjusted position of the reference arm; and
   adjust elements of the first optical system based on the calculated difference such that the sample is visible as the sample is positioned at the working distance of the objective lens of the surgical microscope at the adjusted position of the reference arm.

2. The system of claim 1, wherein the system is further configured to:
   determine whether the imaging system is in focus at the adjusted position of the reference arm before adjusting the elements of the first optical system; and
   adjust the elements of the first optical system upon determining that the system is not in focus until it is determined that the imaging system is in focus.

3. The system of claim 1, wherein the system is further configured to repeatedly adjust the path length of the reference arm of the imaging system, calculate the difference between a current reference arm position and the initial calibrated position and adjust the elements of the first optical system until it is determined that the system is in focus.

4. The system of claim 1, wherein the system is further configured to determine whether the obtained image contains a valid image of the sample based on one of signal quality and features present or absent from the obtained image.

5. The system of claim 1, wherein an imaging plane of the imaging system matches a focal plane of the surgical microscope as the system is in focus.

6. The system of claim 1, wherein the system is further configured to adjust elements of the first optical system by adjusting at least one of a plurality of eye pieces associated with the surgical microscope and other optical components of the first optical system.

7. The system of claim 1, wherein the system is further configured to adjust the position of the reference arm by adjusting a mirror in the reference arm to provide matching optical path lengths in the reference arm and a sample arm of the imaging system and the working distance such that the sample is visible as the sample is positioned at the working distance of the objective lens of the surgical microscope.

8. The system of claim 1, wherein the working distance of the objective lens of the surgical microscope is a distance between the objective lens of the surgical microscope and a surface of the sample.

9. The system of claim 1, wherein the imaging system comprises one of an optical coherence tomography (OCT) imaging system and at least one additional imaging system, different from the first optical system and the second interferometric-based optical system.

10. The system of claim 1, wherein the system is configured to adjust the path length of the reference arm of the imaging system and/or the elements of the first optical system manually.

11. The system of claim 1, wherein the system is configured to adjust the path length of the reference arm of the imaging system and/or the elements of the first optical system automatically.

12. The system of claim 1, wherein the system further comprises:
   a reducing lens between the objective lens and the sample to reduce a focal length of the objective lens; and
   a relay lens adjacent the sample to relay an objective lens image plane to a retina of the sample to adapt the system for imaging the retina of the sample.

13. The system of claim 1, wherein the objective lens is a multifocal objective lens and wherein the system further comprises a relay lens adjacent the sample to relay an objective lens image plane to a retina of the sample to adapt the system for imaging the retina of the sample.

14. A method for optimizing optics of a surgical microscope having an integrated imaging system, the surgical microscope comprising a first optical system, and a second interferometric optical system that is different from the first optical system and associated with the imaging system, the method comprising:
   calibrating a position of a reference arm of the imaging system such that an image of a sample is visible as the sample is positioned at a working distance of an objective lens of the surgical microscope to provide an initial calibrated position;
   obtaining an image using the initial calibrated position of the reference arm of the imaging system;
   assessing image quality of the obtained image to determine whether the obtained image is a valid image;
   adjusting a path length of the reference arm of the imaging system upon determining that the obtained image is not a valid image until it determined that the obtained image is a valid image to provide an adjusted position of the reference arm;
   calculating a difference between the initial calibrated position of the reference arm and the adjusted position of the reference arm; and
   adjusting elements of the first optical system based on the calculated difference such that the sample is visible as the sample is positioned at the working distance of the objective lens of the surgical microscope at the adjusted position of the reference arm.

15. The method of claim 14, further comprising:
   determining whether the imaging system is in focus at the adjusted position of the reference arm before adjusting the elements of the system; and
   adjusting the elements of the first optical system upon determining that imaging system is not in focus until it is determined that the imaging system is in focus.

16. The method of claim 14, further comprising repeating adjusting the path length of the reference arm of the imaging system, and calculating the difference and adjusting the elements of the first optical system until it is determined that the imaging system is in focus.

17. The method of claim 14, wherein the determining whether the obtained image is the valid image is based on one of signal quality and features present or absent from the obtained image.

18. The method of claim 14, wherein an imaging plane of the imaging system matches a focal plane of the surgical microscope as the system is in focus.

19. The method of claim 14, wherein the adjusting the elements of the first optical system comprises adjusting at least one of eye pieces associated with the surgical microscope and other optical components of the first optical system.

20. The method of claim 14, wherein the adjusting the position of the reference arm comprises adjusting a mirror in the reference arm to provide matching optical path lengths in the reference arm and a sample arm of the imaging system and the working distance such that the sample is visible as the sample is positioned at the working distance of the objective lens of the surgical microscope.

21. The method of claim 14, wherein the working distance of the objective lens of the surgical microscope is a distance between the objective lens of the surgical microscope and a surface of the sample.

22. The method of claim 14, wherein the imaging system comprises one of an optical coherence tomography (OCT)

imaging system and additional imaging systems different the first optical system and the second interferometric optical system.

23. The method of claim 14, wherein the adjusting the path length of the reference arm of the imaging system and/or the elements of the first optical system is performed manually.

24. The method of claim 14, wherein the adjusting the path length of the reference arm of the imaging system and/or the elements of the first optical system is performed automatically.

25. The method of claim 14, further comprising:
reducing a focal length of the objective lens using a reducing lens; and
relaying an objective lens image plane to a retina of the sample using a relay lens to adapt the system for imaging the retina of the sample.

26. A non-transitory computer-readable medium having a program code stored thereon, the program code, when executed by a computer processor, causing performance of the method according to claim 14.

* * * * *